United States Patent [19]

Letchworth et al.

[11] 4,155,363

[45] May 22, 1979

[54] ELECTRONICALLY CONTROLLED APPARATUS FOR ELECTROLYTIC DEPILATION

[75] Inventors: Dwight Letchworth, W. Hollywood; Donald A. Colton, Mountain View, both of Calif.

[73] Assignee: International Electrolysis Group Inc., Los Angeles, Calif.

[21] Appl. No.: 915,680

[22] Filed: Jun. 15, 1978

Related U.S. Application Data

[63] Continuation of Ser. No. 716,873, Aug. 23, 1976, abandoned.

[51] Int. Cl.² .................. A61B 17/36; A61N 3/04
[52] U.S. Cl. .................... 128/303.18; 128/419 R
[58] Field of Search .................. 128/303.18, 303.13, 128/303.14, 303.17, 303.15, 172.1, 404, 410, 419 R, 420, 421, 422, 423

[56] References Cited

U.S. PATENT DOCUMENTS

| | | | |
|---|---|---|---|
| 1,858,104 | 5/1932 | Miles | 128/303.18 |
| 3,163,166 | 12/1964 | Brant et al. | 128/172.1 X |
| 3,255,753 | 6/1966 | Wing | 128/421 |
| 3,815,603 | 6/1974 | Sramek | 128/303.18 |
| 3,851,651 | 12/1974 | Icenbice, Jr. | 128/422 |
| 3,866,600 | 2/1975 | Rey | 128/422 X |
| 3,900,020 | 8/1975 | Lock | 128/303.18 X |
| 3,994,300 | 11/1976 | Siddons | 128/303.18 |

*Primary Examiner*—Lee S. Cohen
*Attorney, Agent, or Firm*—John J. Posta, Jr.

[57] ABSTRACT

Apparatus for "depilation" or "electrolysis" including a current source, a plurality of filament electrodes (needles), and electronic circuitry for individually stabilizing the electrode currents at a predetermined value irrespective of withdrawal of selected needles, variations in the effective resistance of the hair and power supply transients.

A programmed current interrupt circuit is also shown, and apparatus for skin conditioning in both current polarities is included, using the basic electronic control circuitry.

9 Claims, 7 Drawing Figures

ELECTRONICALLY CONTROLLED APPARATUS FOR ELECTROLYTIC DEPILATION

This is a continuation of application Ser. No. 716,873, filed Aug. 23, 1976, now abandoned.

BACKGROUND OF THE INVENTION

1. Field of the Invention

The invention relates to devices for human hair destruction and removal by "electrolysis" or "electrolytic depilation".

2. Prior Art

The removal of hair from areas of the human body where it is not desired has long been practiced by chemical, electrical and purely mechanical means. Historically, such hair removal has been more of an art than a science. However, more recently, relatively safe and effective means have evolved. In addition to the mechanical methods, which are not suitable in many cases and are not permanent, there are chemical and electrical methods. Chemical methods may or may not be permanent and, if sufficiently stringent to inhibit regrowth, are likely to produce skin irritations and other medically undesirable effects.

Among the electrical devices for depilation are some which generate and supply light energy in pulsed form to the follicle entrance to produce photoepilation or photocoagulation. Examples of this prior art are found in U.S. Pat. Nos. 3,693,623 and 3,834,391.

A prior art U.S. patent more germane to the specific type of electrolytic depilatory device of the invention is U.S. Pat. No. 3,815,603. In that reference a unidirectional current with a superimposed radio frequency component or modulation is applied through a well known filament electrode to destroy the papilla associated with the root of the hair to be destroyed.

The flow of the unidirectional current by itself is known to be effective in destroying the papilla chemically by dissociating tissue water into hydrogen cations and hydroxide anions in the immediate vicinity of the papilla (galvanic electrolysis). To insure a suitable charge concentration, such electrolytic depilatory devices customarily employ a "wet pad" or body electrode in electrical contact with an adjacent part of the body as a positive electrode. The filament electrode or needle is the negative electrode, and the depilatory action is then a function of the current-time integral.

Discomfort associated with electrolytic (galvanic) depilation is generally in proportion to the effectiveness of the action.

In describing the invention hereinafter, a prior art depilation circuit employing a number of filamentary electrodes (needles) is described as background. Practical devices of the type generally use multiple needles. Therein lies the source of an additional problem; namely, the unequal division of current among the plural needles when a common current source is employed. This is true even if a constant current source is employed as suggested in the aforementioned U.S. Pat. No. 3,815,603.

That, and other disadvantages of the prior art are uniquely remedied by the combination of the invention, as will be described hereinafter.

SUMMARY OF THE INVENTION

The device of the invention provides galvanic electrolysis through a plurality of filamentary electrodes (needles) with discrete current stabilization for said needles.

According to the invention, a source of direct current is supplied through a voltage regulator to a bank of constant current devices, and alternatively to a polarity reversing switching arrangement for alternative operation in a skin condition mode. Another embodiment provides for programmed polarity reversal of a potential applied between the body electrode and a conditioning roller for separate operation as a skin conditioner.

The bank of constant current devices corresponds, on a one-for-one basis, to the plurality of needles, accordingly body resistance differences, insertion and withdrawal of various needles and source variations do not affect the individual predetermined needle currents.

For purposes of description, four modes of operation are identified as follows:

Mode I—Galvanic electrolysis with current stabilization to individual electrodes (uninterrupted).

Mode II—Galvanic electrolysis with individual electrode current stabilization and with programmed periodic current interruption.

Mode III—Negative skin conditioning.

Mode IV—Positive skin conditioning.

A very important aspect of the present invention is the individual needle current stabilization circuits.

The details of the manner in which the present invention may be typically instrumented are described hereinafter with reference to the drawings.

DRAWINGS

DETAILED DESCRIPTION

Figure 1A:
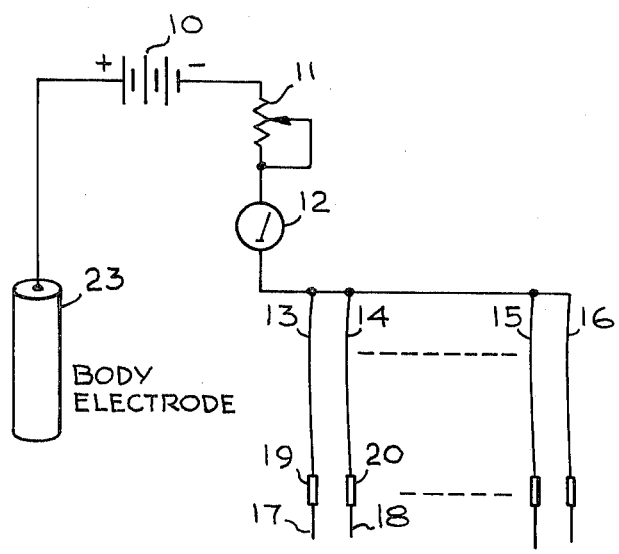
FIG. 1(a) is a typical multiple needle prior art electrolytic depilation device.

Referring now to FIG. 1(a), a typical prior art multi-needle (plural filamentary electrodes) device of the type which the present invention greatly improves is depicted. A battery, or other current source 10 provides a current from its negative pole through a variable resistance 11 for current control. A microammeter 12 facilitates current adjustment.

However, the current cannot be presumed to be equally divided among the plural needles, i.e., among leads 13, 14, 15 and 16 as well as the others of the plurality. This is basically because of varying ohmic resistance within the body tissues as presented at the needles (typically 17 and 18).

Moreover, withdrawal and reinsertion of needles, as is commonly done during treatment, disturbs the current distribution as well as the total parallel current value.

The insulated enlargements (19 and 20, for example) are purely for operator convenience in handling the needles.

Figure 1B:
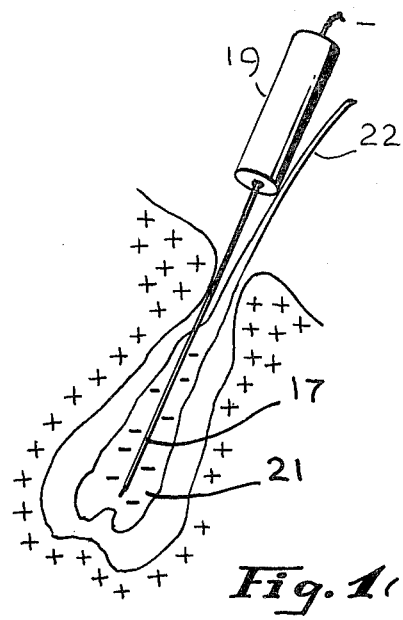
FIG. 1(b) is an exaggerated representation of a needle of an electrolytic depilation device inserted in the proximity of the papilla associated with a hair root.

FIG. 1(b) depicts a much enlarged hair root area, the so-called papilla being associated with the root 21 of hair 22. A needle 17, negatively poled is as identified in FIG. 1(a). The body electrode 23 provides the return for all parallel probe currents.

This body electrode is normally attached to the body, usually near the treatment area and is sometimes referred to as a "wet pad". Variations in the location and resistance of the body electrode contact can obviously adversely affect total needle current and division of current among the needles.

It is known that the hair destroying effect of the electrolysis occurring about the papilla is a function of the current-time product. Lower currents take longer to produce their effect, but discomfort on the other hand is greater at higher current values.

Variation above a nominal selected current as a result of factors hereinbefore discussed can increase discomfort and even require that treatment current be lower than optimum so that withdrawal of needles and other variation causes will not produce momentarily unnecessarily high current in a needle or needles.

Figure 2:
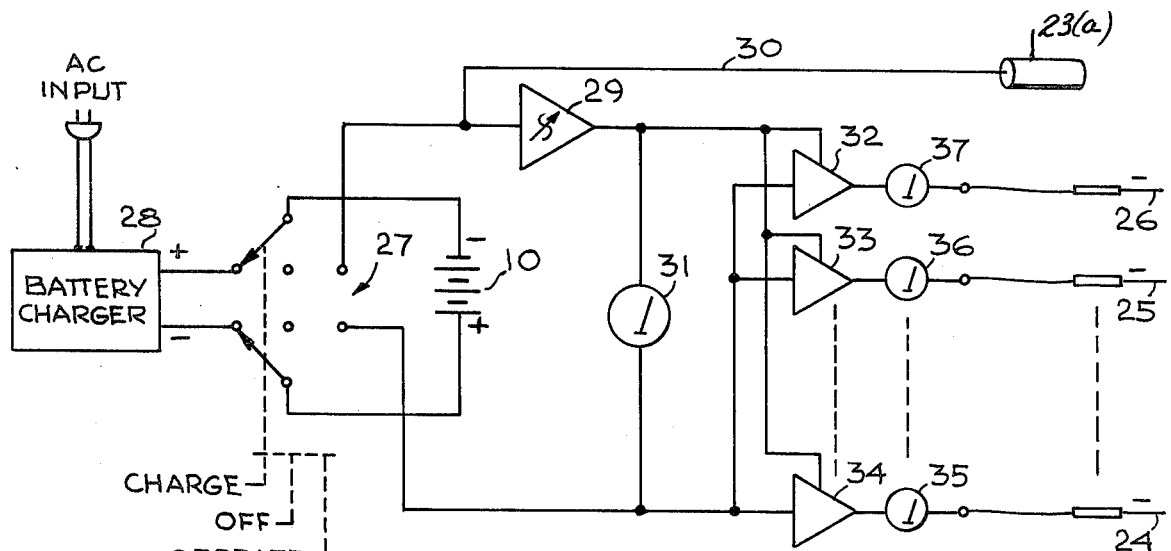
FIG. 2 is a schematic block diagram of a first embodiment according to the invention for Modes I, III and IV operation.

Referring now to FIG. 2, a first embodiment according to the invention shows partial similarity to FIG. 1(a) in that the battery 10 and typical needles 24, 25 and 26, substantially identical with 17 and 18 are used. Also included is a body electrode 23(a) which is connected to power source 10 via circuit 30.

A double-pole, triple-throw switch 27 provides for switch-over from charge to operate positions and also includes an off position. As illustrated, the battery 10 is on charge and the device cannot operate otherwise. Battery charger 28 is entirely straightforward and well known in the prior art.

The center position of switch 27 is "off", and the right throw is "operate", with the battery 10 powering the circuitry accordingly. It is important that "charge" and "operate" be thus isolated from each other, so that line transients or failures in 28 cannot subject the patient to unusually high, and possibly dangerous, currents from the higher potentials of the AC supply.

The internal resistance variations of battery 10 as a function of discharge and current variations are eliminated through the use of voltage regulator 29. This regulator is illustrated in typical form in FIG. 6.

Figure 6:
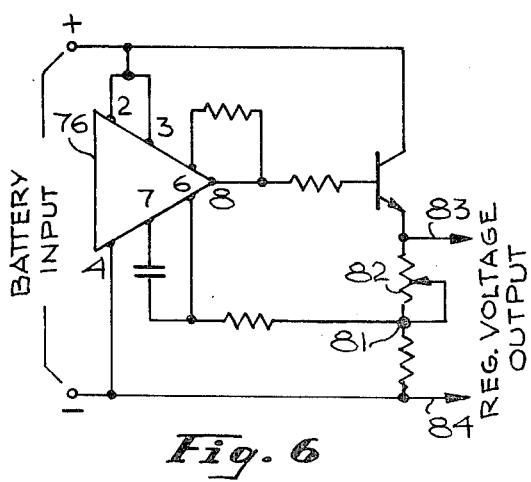
FIG. 6 is a schematic diagram of a typical solid-state voltage regulator as shown in FIGS. 2 through 4.

It will be seen that a regulated voltage appears across the terminals of voltmeter 31, this voltage being adjustable within the regulator circuit of FIG. 6. The voltage at the terminals of voltmeter 31 is typically on the order of 12 volts, and this constitutes the stable supply potential fed in parallel to a plurality of discrete current regulators (stabilizers), typically 32, 33 and 34. The current through each of these regulators is predetermined by the circuit constants of a current regulator circuit, can be made adjustable and typically is set within the range of 20 to 200 microamperes.

Figure 5:
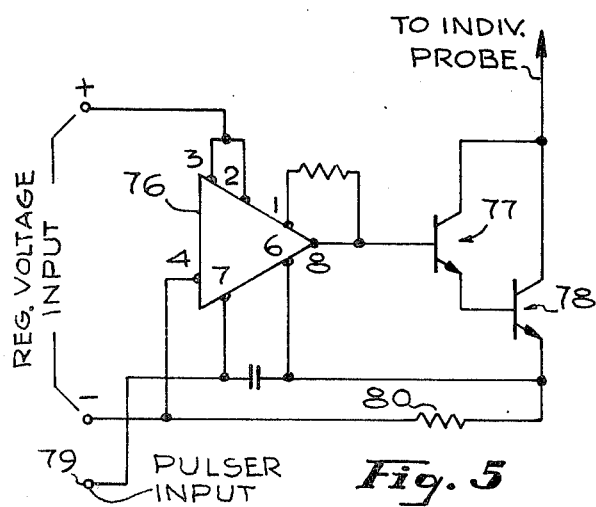
FIG. 5 is a schematic diagram of a typical solid-state current regulating circuit as found in FIGS. 2 and 3.

Needles 24, 25 and 26 are identical to their FIG. 1(a) counterparts and each is preferably fed through a series microammeter 35, 36, and 37 respectively, for monitoring or adjustment. The details of typical circuitry for the regulator units 32, etc., are shown in FIG. 5.

Figure 3:
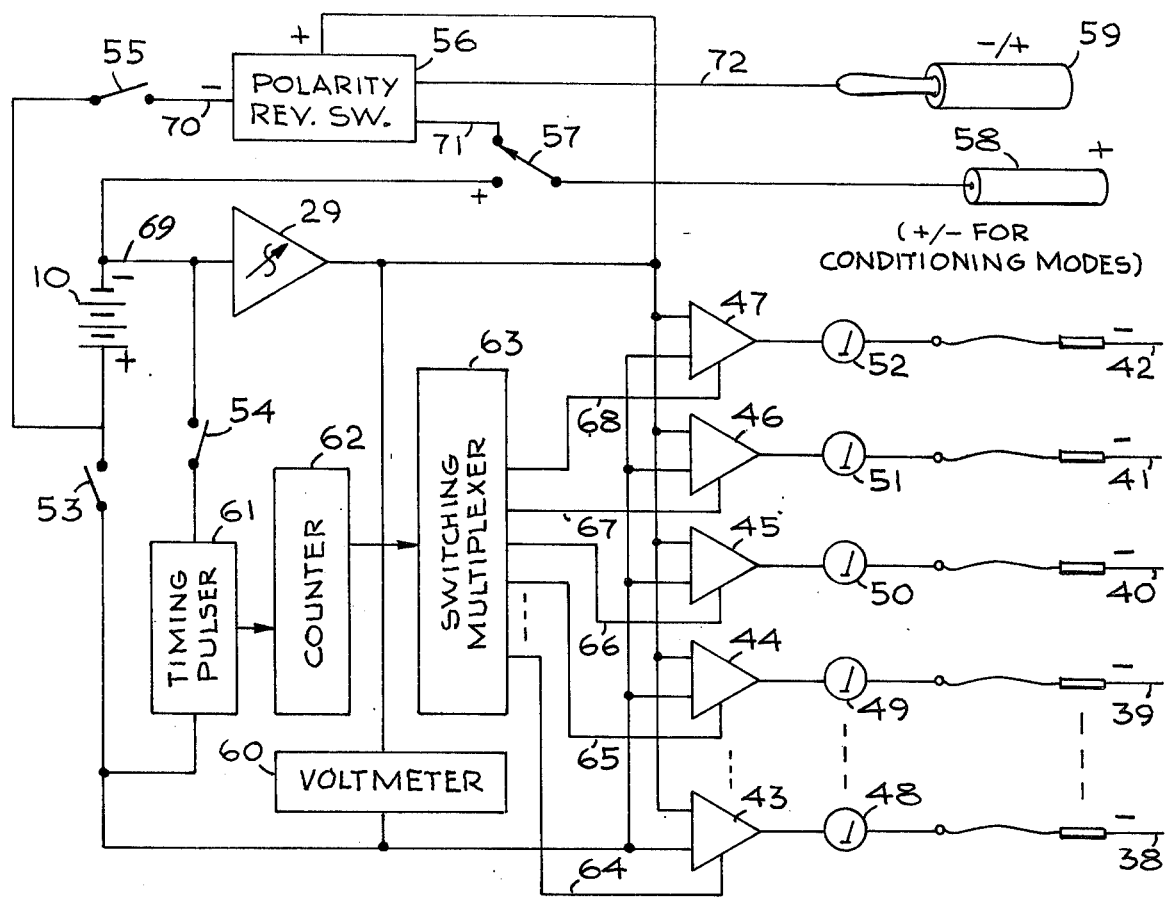
FIG. 3 is a schematic block diagram of a second embodiment for Mode II operation.

Referring now to FIG. 3, a circuit for Modes II, III and IV operation will be described. It is to be understood that the battery charger and charge/operate switching arrangement of FIG. 2 can be incorporated into FIG. 3.

A switch 53 provides an overall on/off control for the circuits of FIG. 3, and a voltage regulator 29 substantially identical with 29 of FIG. 2 is provided. Voltmeter 60 is identical to 31 of FIG. 2 and may be any known type, including digital, and the same stabilized voltage (approximately 12 volts typically) appears across 60, this supplying the plural discrete current regulators 43, 44, 45, 46 and 47. These current regulators are also shown in FIG. 5. A gating control input or pulser control (FIG. 5), not used in FIG. 2 is controlled by switching multiplexer 63, via leads 64, 65, 66, 67 and 68 as shown. A counter 62 controlled by a timing pulser 61, activated by switch 54 places the current interrupt feature of Mode II in operation.

The device 63 is no more than a sequential "distributor" and as such is readily constructed by the skilled practitioner of the electronic circuit arts. Basically, each needle current is interrupted for a time on the order of 1 to 3 seconds (one needle at a time) out of the 40 to 60 second typical electrolysis (subject to operator and design discretion).

The needles 38, 39, 40, 41 and 42 are monitored by microammeters 48, 49, 50, 51 and 52, respectively, as shown, this arrangement repeating that of FIG. 2.

The body electrode 58 is, as before, poled positive and switch 57 is in the down position (the other position than shown in FIG. 3).

When switch 55 is closed, for operation in Modes III and IV (skin conditioning), the switch 57 is switched as illustrated, and the regulated voltage between leads 69 and 70 is available to the polarity reversing switch 56. The output leads 71 and 72 from 56 thus are interchanged polarity-wise by operation of the internal switching within 56. Thus, the conditioning roller 59 may be positive or negative selectively, with respect to body electrode 58.

Figure 4:
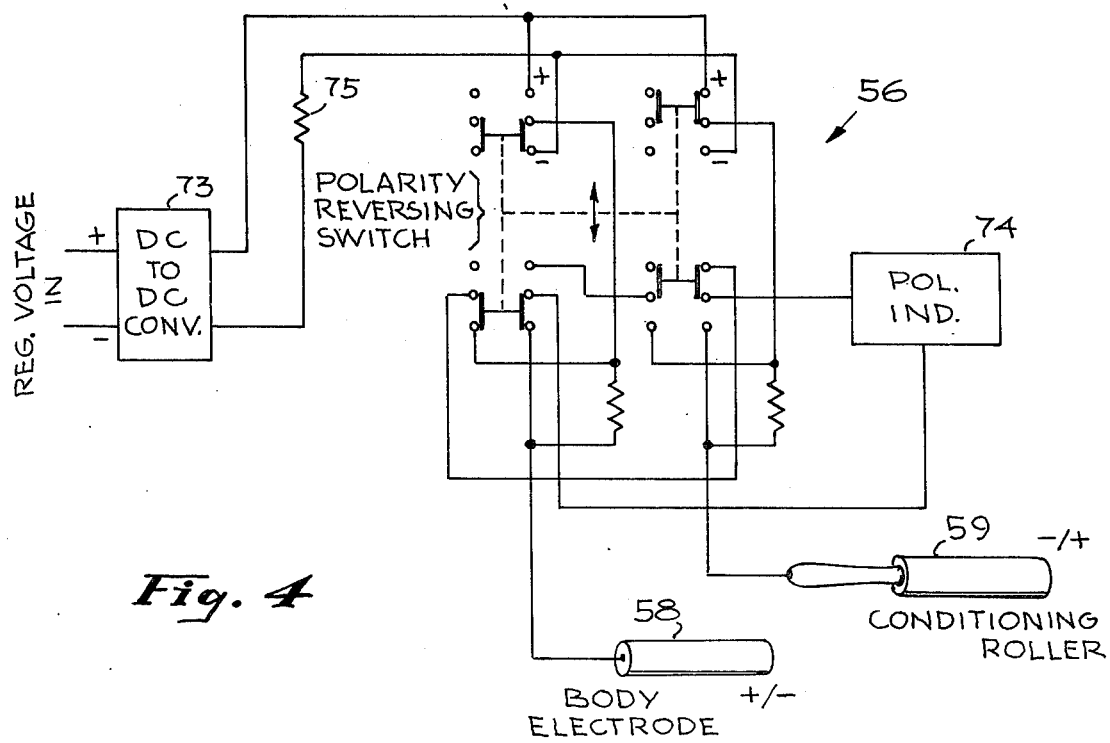
FIG. 4 is a schematic block diagram illustrating the operation of the polarity reversing switch of FIG. 2 for Modes III and IV operation.

Referring now to FIG. 4, a largely self-explanatory reversing switch arrangement is depicted. A dc-to-dc converter 73 provides the higher voltage required in Modes III and IV (up to approximately 65 volts), and a polarity indicator 74 monitors the polarity at any time.

Current limiting is provided by resistance 75 such that no more than 500 microamperes can flow in the conditioning function.

FIGS. 5 and 6 will be recognized as straightforward solid state circuits. Each includes an integrated circuit gain element 76, typically a CA-3085 (manufactured by RCA). NPN transistors 77 and 78 handle the needle current in FIG. 5 and pulser input 79 receives the Mode II gating control (for current interruption) as shown in FIG. 3. The terminal 79 is unused in the FIG. 2 arrangement (Mode I).

A feedback term derived as a function of current through resistor 80 provides the inverse feedback control in FIG. 5 to produce the regulating action.

In FIG. 6, the feedback term arises at junction 81 and adjustment of variable resistance 82 effects adjustment of the regulated voltage between terminals 83 and 84.

The circuits of FIGS. 5 and 6 will be recognized by those skilled in electronic circuits, and obviously are subject to considerable design variation.

Other variations and modifications will suggest themselves to those skilled in the related arts, once the principles of the invention are understood. Accordingly, the drawings and this description are to be recorded as typical and illustrative only.

What is claimed is:

1. An improved electrical depilation device for electrochemically destroying hair papilla by galvanic electrolysis comprising:
   a direct current power source,
   a first electrode means for conducting electric current below the surface of the skin of a subject in the vicinity of a first papilla,
   a second electrode means for conducting electric current below the surface of the skin of said subject in the vicinity of a second papilla,
   a wet pad electrode adapted to contact the subject's skin for conducting current between the first and second electrode means and the wet pad electrode,
   a first circuit interconnecting the power source to said first and second electrode means,
   a second circuit interconnecting the power source to said wet pad electrode,
   said first circuit having included therein a first adjustable voltage regulator means capable of maintaining a variable, pre-selected voltage in said first circuit,
   means for varying the voltage in said first circuit,
   first adjustable current regulator means connected to said first electrode means and capable of maintaining a variable and pre-selected current in said first electrode means, second adjustable current regulator means connected to said second electrode means and capable of maintaining a variable and pre-selected current in said second electrode means,
   means for varying the current regulating level of each said first and second current regulator means,
   said first and second current regulator means being capable of maintaining the passage of a pre-selected current to the electrode means to which it is directly connected despite variations in the amount of current, if any, flowing in the electrode means to which it is not directly connected,
   whereby said device can be pre-set to operate at a pre-selected voltage level with pre-selected current levels passing through each electrode means, which current and voltage levels will be maintained in each operative electrode means irrespective of changes in current or voltage levels in the other electrode means.

2. The depilation device of claim 1 and further including means for measuring the voltage level in the first circuit and the current levels passing through each of the first and second electrode means.

3. The depilation device of claim 2 wherein said power source is an electro-chemical battery.

4. Apparatus according to claim 3 in which said battery is rechargeable, in which a battery charger is included, and in which first switching means are included for connecting said battery exclusively to said charger and alternatively to said voltage regulator means exclusive of any connection with said charger, thereby to foreclose operation of said first and second electrode means during battery charging.

5. Apparatus according to claim 1 including means for periodically interrupting said currents in each of said first and second electrode means according to a predetermined program.

6. Apparatus according to claim 5 including means for effecting said programmed current interruption of said first and second electrode means currents to one of said first and second electrode means at a time, the current on-time being relatively large compared to the off-time in any one of said first and second electrode means.

7. Apparatus according to claim 6 in which said means for programmed current interruption comprises a circuit means for controlling said first and second current regulator means to cause them to operate between a predetermined value of stabilized current for a first time interrupted by a zero current condition at predetermined intervals.

8. Apparatus according to claim 7 in which said circuit means for controlling said first and second current regulator means comprises a timing pulser, a counter circuit, a switching multiplexer, and circuit means interconnecting said timing pulser, counter circuit and multiplexer, said counter circuit determining the time and duration of each current interruption, and said multiplexer being responsive to said counter circuit to successively select the one of said first and second current regulator means to be subjected to said zero current condition at any time.

9. Apparatus according to claim 1 and further including an electrically conductive conditioning roller adapted to contact the skin of the subject,
   a polarity reversing switch having a pair of output terminals,
   and switching circuit means for alternatively connecting said power source and voltage regulator means to said polarity reversing switch and conditioning roller instead of to said first and second current regulator means whereby said output terminals provide reversible polarity current for application between the wet pad electrode and said conditioning roller.

* * * * *